United States Patent [19]

Falk

[11] 4,212,203

[45] Jul. 15, 1980

[54] MOLTEN METAL STREAM SAMPLER WITH FILL GAUGE

[76] Inventor: Richard A. Falk, 519 Westminster Dr., Waukesha, Wis. 53186

[21] Appl. No.: 31,569

[22] Filed: Apr. 19, 1979

[51] Int. Cl.² .............................................. G01N 1/12
[52] U.S. Cl. ................................................. 73/425.4 R
[58] Field of Search ...................... 73/425.4 R, DIG. 9

[56] References Cited

U.S. PATENT DOCUMENTS

| | | | |
|---|---|---|---|
| 3,915,002 | 10/1975 | Hance | 73/425.4 R |
| 3,994,172 | 11/1976 | Kelsey | 73/425.4 R |
| 3,996,803 | 12/1976 | Falk | 73/425.6 |
| 4,051,732 | 10/1979 | Falk | 73/425.4 R |
| 4,069,717 | 1/1978 | Falk | 73/425.4 R |

Primary Examiner—S. Clement Swisher
Attorney, Agent, or Firm—Henry C. Fuller

[57] ABSTRACT

A stream sampler includes a cylindrical refractory wall with an elongated fill tube held in place against the inner surface of the wall by one or more refractory struts and a sight gauge which indicates the quantity of metal in the mold cavity.

3 Claims, 2 Drawing Figures

MOLTEN METAL STREAM SAMPLER WITH FILL GAUGE

BACKGROUND OF THE INVENTION

Various stream samplers have been developed to take a sample of molten metal flowing from a stream. My patents, U.S. Pat. No. 3,996,803; 4,051,732; and 4,069,717 are illustrative of stream samplers. Stream samplers disclosed in these patents all have sample forming walls to form a disc shaped sample which is suitable for spectrographic analysis. The present invention provides a stream sampler which molds a large quantity of metal into a cylindrical shaped sample, which disc is subsequently sliced or cut to form numerous samples.

SUMMARY OF THE INVENTION

The invention provides a molten metal stream sampler which includes a refractory wall defining a sample cavity, with a fill tube which is supported on the inner surface of the cylindrical wall and is anchored there by a refractory rod or strut which spans the distance between the fill tube and opposite refractory wall and is secured in place by refractory cement. A sight or fill gauge can also be employed to assist in securing the fill tube in place in addition to providing a visual indication that the cylindrical mold cavity has been filled. The fill gauge projects through an opening in the refractory wall and is cemented in place. The inner end of the sight gauge is in contact with the fill tube but the inside tubular opening of the fill gauge tube is large enough to permit entry of molten metal which will rise in the tube as the sample cavity fills.

Further objects, advantages and features of the invention will become apparent from the disclosure.

DESCRIPTION OF THE PREFERRED EMBODIMENT

Figure 1:
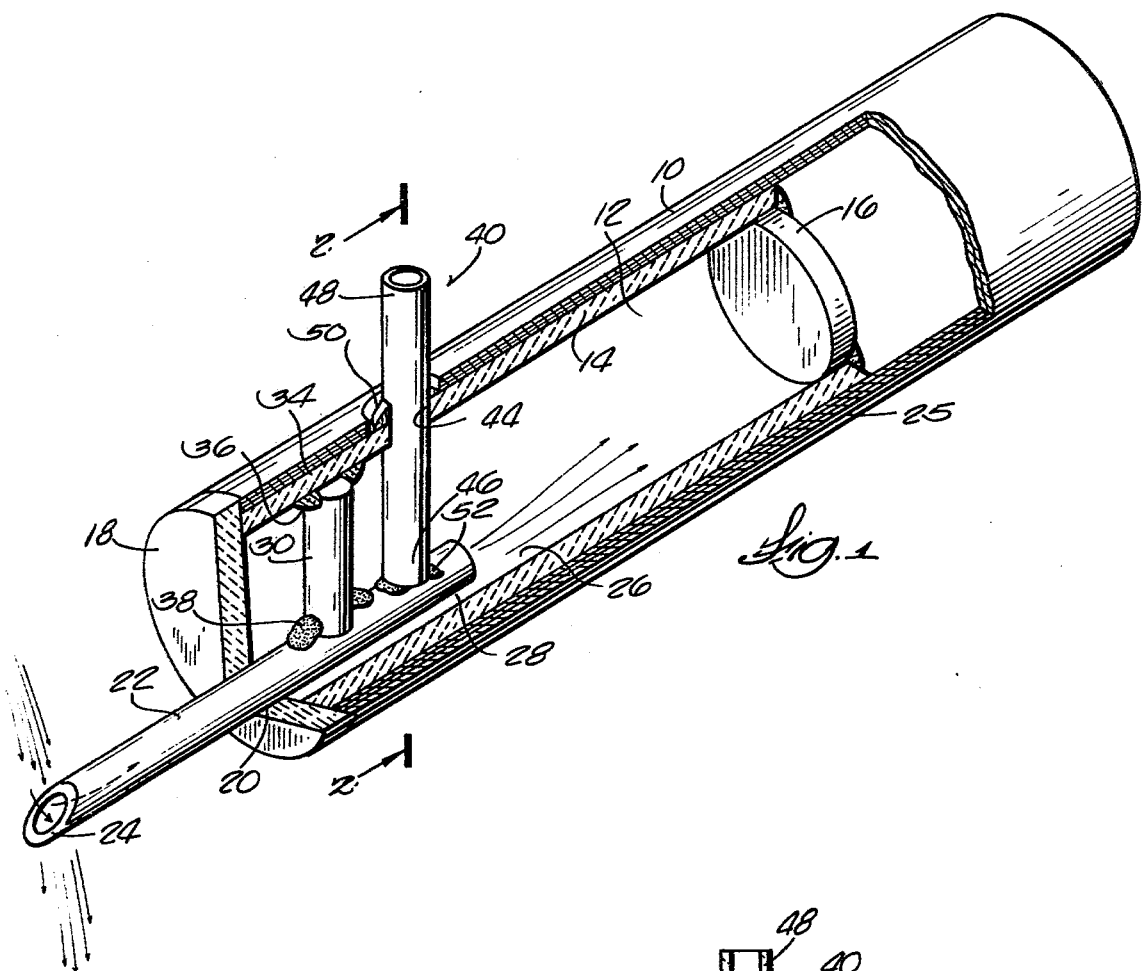
FIG. 1 is a perspective view of a sampler in accordance with the invention.

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

The sampler 10 has a mold cavity 12 defined by a cylindrical refractory wall 14 provided with end walls 16 and 18 which can be constructed of refractory or refractory fibers. End wall 18 is provided with an aperture 20 for a fused quartz or heat resistant fill tube 22 which can be provided with a beveled tip 24 for use as a stream sampler. The refractory wall can be enclosed by a paperboard sleeve 25.

The fill tube 20 is supported by the inside surface 26 of refractory wall 14 and secured in tangential contact thereto by beads of refractory cement 28. Further support for the fill tube 20 is provided by a refractory strut 30 which is wedged between the tube 22 and the refractory wall portion 34. The strut is cemented by refractory cement at 36 and 38.

Figure 2:
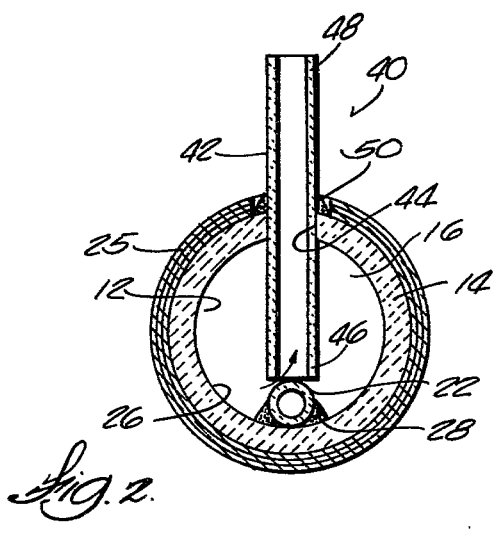
FIG. 2 is a sectional view along line 2—2 of FIG. 1.

The sampler can also include a sight gauge 40 in the form of a transparent fused quartz or glass tube 48 which extends through an opening 44 in the refractory wall 14 and has one end 46 in supporting contact with the tube 22 and the outer end 48 located remote from the tube. The tube 42 can be fixed in place by refractory cement 50 and 52, in which case it also provides support for the fill tube 22. As illustrated in FIG. 2, molten metal can flow inside tube 48 into the bore 50 over the surface of tube 22 because of the clearance, as illustrated, and provide a visual indication of the quantity of metal in the mold cavity 12.

I claim:

1. A molten metal stream sampler including a refractory cylindrical wall defining a mold cavity, a fill tube extending into said cavity, and means for securing said fill tube along the inside surface of said cylindrical wall, said means including a strut extending at right angles with the longitudinal fill tube axis and wedged between said fill tube and the opposite refractory wall in spanning relation across said mold cavity, and refractory cement at the ends of said strut and said fill tube securing the strut and said fill tube on said refractory cylindrical wall.

2. The sampler of claim 1 including a sight gauge having an inner end abutting said fill tube, an opening in said refractory wall, and said sight gauge extending through said wall and having an outer end remote from said refractory wall, and refractory cement securing said tube to the refractory wall and to said fill tube.

3. A molten metal stream sampler including a refractory cylindrical wall defining a mold cavity, a fill tube extending into said cavity, a sight gauge having an inner end abutting said fill tube, a side opening in said refractory wall, and said sight gauge extending through said wall into said cavity in a direction transverse to said fill tube to receive molten metal from said cavity and provide an indication of the extent of metal in said cavity, and refractory cement securing said tube to the refractory wall.

* * * * *